United States Patent [19]

Doss

[11] 3,985,673

[45] Oct. 12, 1976

[54] STABILIZATION OF MIXTURES OF MERCAPTOALKYLNITRILES AND THIODIALKYLNITRILES

[75] Inventor: Richard C. Doss, Bartlesville, Okla.

[73] Assignee: Phillips Petroleum Company, Bartlesville, Okla.

[22] Filed: Oct. 16, 1975

[21] Appl. No.: 623,122

[52] U.S. Cl. ............................ 252/182; 252/400 A; 260/45.7 P; 260/76
[51] Int. Cl.² ...................... C09K 15/32; C08K 5/36
[58] Field of Search .................... 252/182, 400 A; 260/45.7 P, 76, 30.6 R

[56] References Cited
UNITED STATES PATENTS

| | | | |
|---|---|---|---|
| 2,419,354 | 4/1947 | Howland et al. | 260/45.7 P |
| 2,733,226 | 1/1956 | Hunter | 260/45.7 P |
| 3,255,151 | 6/1966 | Hecker et al. | 260/45.7 P |
| 3,817,936 | 6/1974 | Jones et al. | 260/76 |
| 3,888,817 | 6/1975 | Georgoudis | 260/45.7 P |

Primary Examiner—Benjamin R. Padgett
Assistant Examiner—Irwin Gluck

[57] ABSTRACT

Mixtures of mercaptoalkylnitriles and the corresponding thiodialkylnitriles are stabilized by incorporating therein a stabilizing amount of an organic phosphite of the formula

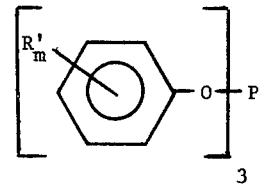

wherein R' is hydrogen or alkyl having from 1 to 20 carbon atoms and m is an integer having a value of 1 or 2. The above mixture is hydrolyzed to the corresponding carboxylic acids for use in preparing poly(oxyalkylene)-polyester-poly(monosulfide)-polythiol polymers.

16 Claims, No Drawings

STABILIZATION OF MIXTURES OF MERCAPTOALKYLNITRILES AND THIODIALKYLNITRILES

This invention relates to the stabilization of mixtures of mercaptoalkylnitriles and the corresponding thiodialkylnitriles.

Sealant and caulking compositions based upon polythiol compounds are of considerable industrial importance. U.S. Pat. No. 3,817,936, issued June 18, 1974 to Jones and Marrs discloses a poly(oxyalkylene)-polyester-polymonosulfidepolythiol composition prepared from a. a mercaptoalkanoic acid having the formula

HS - (CR$_2$)$_n$COOH wherein R is selected from the group consisting of hydrogen and alkyl groups having from 1 to 5 carbon atoms, the maximum number of carbon atoms in all R groups being 10, and n is an integer ranging from 1 to 5, b. a thiodialkanoic acid having the formula

HOOC — (CR$_2$)$_n$ — S — (CR$_2$)$_n$ - COOH wherein R and n are as defined above, the maximum number of carbon atoms in all R groups being 20, and c. a poly(oxyalkylene)-polyol having at least three pendent hydroxy groups per molecule and a molecular weight in the range of 200–20,000.

The mercaptoalkanoic and thiodialkanoic acids are prepared by hydrolysis of the corresponding nitriles. These nitriles are prepared by the reaction of the corresponding unsaturated nitriles with hydrogen sulfide. For example, acrylonitrile can be reacted with hydrogen sulfide to form a mixture of 3-mercaptopropionitrile and 3,3'-thiodipropionitrile. Since both the mono- and dicarboxylic acids are employed in the preparation of the above-described polythiol, it is generally unnecessary to separate the mono- and dinitriles prior to the hydrolysis operation.

The mixture of the mercaptoalkylnitrile and the thiodialkylnitrile is, however, unstable, and will undergo spontaneous polymerization during storage. Prior to this invention the mixture was stabilized by the addition of para-toluenesulfonic acid, which stabilized the mixture sufficiently to allow storage under refrigeration. However, due to the cost of refrigeration, it is desirable to be able to store this mixture at ambient conditions prior to use.

It is therefore an object of this invention to provide a stabilized mixture of a mercaptoalkylnitrile and a thiodialkylnitrile which can be stored at ambient temperature.

It is another object of this invention to provide a method for stabilizing a mixture of a mercaptoalkylnitrile and a thiodialkylnitrile.

Other objects, aspects and advantages of the present invention will be readily apparent to those skilled in the art from a study of this disclosure and appended claims.

I have discovered that the addition of an organic phosphite to a mixture of a mercaptoalkylnitrile and a thiodialkylnitrile stabilizes the mixture such that the mixture can be stored at ambient temperature.

More particularly, a crude mixture of a. a mercaptoalkylnitrile of the formula

HS — (CR$_2$)$_n$ — CN wherein R is hydrogen or an alkyl group having from 1 to 5 carbon atoms, the maximum number of carbon atoms in all R groups being 10, and n is an integer having a value of 1 to 5, and b. the corresponding thiodialkylnitrile having the formula

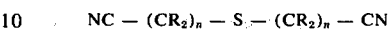
NC — (CR$_2$)$_n$ — S — (CR$_2$)$_n$ — CN wherein R and n are as described above, the maximum number of carbon atoms in all R groups being 20, can be stored at ambient temperature when having incorporated therein a stabilizing amount of an organic phosphite of the formula

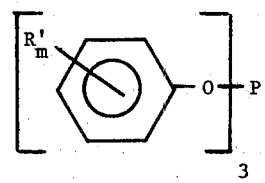

wherein each R' is individually selected from the group consisting of hydrogen and alkyl having from 1 to 20 carbon atoms, preferably from 6 to 12 carbon atoms, and m is an integer having a value of 1 or 2. The R' group can be in any position on the aromatic ring relative to the oxygen. It is presently preferred that R' be alkyl, in the para position. The phosphite can contain from 18 to 60 carbon atoms, with 36 to 50 carbon atoms per molecule being preferred. The unspecified positions of the aromatic ring are occupied by hydrogen.

Examples of organic phosphites useful in the practice of this invention include triphenyl phosphite, tri-p-tolyl phosphite, tris(4-n-propylphenyl) phosphite, tris(2-n-hexylphenyl) phosphite, tris(4-n-nonylphenyl) phosphite, tris(4-n-tetradecylphenyl) phosphite, diphenyl-4-n-eicosylphenyl phosphite, and the like, and mixtures thereof.

In a presently preferred embodiment the organic phosphite is tris(4-n-nonylphenyl) phosphite.

Examples of mixtures of mercaptoalkylnitriles and thiodialkylnitriles that can be stabilized according to the present invention include:

mercaptoacetonitrile/thiodiacetonitrile,
3-mercaptopropionitrile/3,3'-thiodipropionitrile,
4-mercaptobutyronitrile/4,4'-thiodibutyronitrile,
6-mercaptohexanenitrile/6,6'-thiodihexanenitrile,
6-mercaptoundecanenitrile/6,6'-thiodiundecanenitrile,
6-mercapto-6-(2,2-dimethylpropyl) undecanenitrile/bis[5-(1-cyano-5-(2,2-dimethylpropyl)decyl] sulfide,
2-mercapto-2-methylheptanenitrile/bis[2-(2-cyanoheptyl)] sulfide,
3,3-dimethyl-6-mercapto-hexanenitrile/bis[5-(1-cyano-2,2-dimethylpentyl)] sulfide, and
6-mercapto-2,2,3,3,4,4,5,5,6-nonamethylheptanenitrile/bis[6-(2-cyano-2,3,3,4,4,5,5,6-octamethylheptyl)] sulfide,
and the like.

These mixtures of compounds can be prepared by the addition of hydrogen sulfide to olefinically unsaturated nitriles. Frequently accompanying these major products of the reaction are minor products such as disulfides, isomeric mercaptoalkylnitriles and isomeric thiodialkylnitriles. Such minor products need not be removed from the mixture of major products for treatment of the latter with the organic phosphites for inhibition of polymerization.

Mixtures of the above-described mercaptoalkylnitriles and thiobis(alkylnitriles) which can be stabilized according to the present invention are those in which the weight ratio of the mercapto compound to the thioether compound is in the range of 99:1 to 1:99, preferably from 60:40 to 90:10.

The above-described organic phosphites are added to the mixtures of mercaptoalkylnitrile and thiobis(alkylnitrile) in any manner which provides substantially uniform dispersion and in an amount sufficient to provide the desired degree of polymerization inhibition during storage. The amount of organic phosphite to be used will vary according to the compounds to be stabilized, storage conditions, and the like. The stabilized mixture can be stored either in the presence or absence of air. Storage temperatures in the range of $-18°$ C or lower to $38°$ C or higher can be employed; however, it will be appreciated by one skilled in the art that as storage temperature is increased, maximum storage lifetime decreases. Maximum storage lifetime is defined as the time after which sufficient spontaneous polymerization occurs to render the mixture discolored and excessively viscous. Accordingly, while storage temperatures considerably above $38°$ C can be employed, the maximum storage lifetime of the mixture will be reduced.

The organic phosphite is added to the mixture of mercaptoalkylnitrile and thiodialkylnitrile in an amount sufficient to stabilize the mixture at ambient conditions.

Generally, from about 0.01 to about 5 weight percent of the organic phosphite, based upon the weight of the above-described mixture, is sufficient to provide the desired storage stability. In a presently preferred embodiment, the amount of organic phosphite employed is in the approximate range of 0.1 to 3 weight percent.

The stabilized mixtures of mercaptoalkylnitriles and thiobis(alkylnitriles) are employed in the preparation of polythiol-based sealant compounds in the same manner in which the uninhibited mixtures are employed, as described in U.S. Pat. No. 3,817,936.

The following example illustrates the invention.

EXAMPLE

The crude reaction product from the reaction of hydrogen sulfide with acrylonitrile, prepared as described in U.S. Pat. No. 3,817,936 and containing 67.3 percent 3-mercaptopropionitrile, 26.5 percent 3,3'-thiodipropionitrile, minor amounts of other products and 1 weight percent p-toluene sulfonic acid, was tested as described below for stability under storage conditions at about $24°$ C. The percentages given above are area percents calculated as percent of total peak area of components eluting through a gas-liquid chromatograph.

To 45-gram portions of the above-described fluid mixture was added 0.45 gram of the additives given in the following table. The fluid mixture originally had a yellowish-green color. These test portions were stored at room temperature (about $24°$ C) for extended periods. The results of visual observation during aging are given in the following table:

Table

| Run No. | 1 | 2 | 3 |
|---|---|---|---|
| Additive | None | 2,2-Methylene bis(4-methyl-6-t-butyl-phenol) | Tris(4-n-nonylphenyl) phosphite |
| Observation Time (days) | | | |
| 0 | No change | No change | No change |
| 48 | Red | Dark red | No change |
| 64 | Very dark red; viscous | Very dark red, viscous | No change |
| 94 | Not observed | Not observed | Dark red |

It can be seen from a consideration of runs 1 and 2 that the course of color change of the above-described mixture goes from yellowish-green to red to dark red to very dark red as the mixture undergoes polymerization, as indicated by the apparent increase in viscosity. The organic phosphite of this invention provided storage stability for at least 64 days, while the unstabilized mixture of run 1 and the mixture containing the hindered phenol of run 2 commenced spontaneous polymerization at some time between 0 and 48 days.

Reasonable variations and modifications, which will be apparent to those skilled in the art, can be made in this invention without departing from the spirit and scope thereof.

What is claimed is:
1. A method for stabilizing a mixture of
A. a mercaptoalkylnitrile of the formula

$$HS - (CR_2)_n - CN$$

wherein each R is individually selected from the group consisting of hydrogen and alkyl groups having from 1 to 5 carbon atoms, the maximum number of carbon atoms in all the R groups being 10, and n is an integer having a value of 1 to 5, and
B. the corresponding thiodialkylnitrile of the formula $$NC - (CR_2)_n - S - (CR_2)_n - CN$$

wherein R and n are as defined above, the maximum number of carbon atoms in all the R groups being 20, the weight ratio of said compound (A) to said compound (B) being in the range of 99:1 to 1:99, which consists of incorporating with said mixture a stabilizing amount of an organic phosphite of the formula

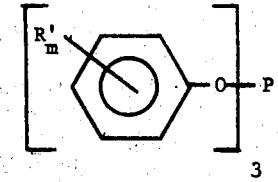

wherein R' is individually selected from the group consisting of hydrogen and alkyl groups having from 1 to 20 carbon atoms, and m is an integer having a value of 1 or 2.

2. The method of claim 1 wherein the amount of said organic phosphite incorporated with said mixture is in the approximate range of 0.01 to 5 weight percent.

3. The method of claim 1 wherein the weight ratio of said compound (A) to said compound (B) is in the approximate range of 60:40 to 90:10.

4. The method of claim 1 wherein said R' is alkyl.

5. The method of claim 1 wherein said R' is selected from the group consisting of hydrogen and alkyl groups of from 6 to 12 carbon atoms.

6. The method of claim 5 wherein said R' is alkyl.

7. The method of claim 6 wherein said organic phosphite is tris(4-n-nonylphenyl) phosphite.

8. The method of claim 1 wherein said compound (A) is 3-mercaptopropionitrile and said compound (B) is 3,3'-thiodipropionitrile.

9. A stabilized composition consisting essentially of a mixture of
A. a mercaptoalkylnitrile of the formula

wherein each R is individually selected from the group consisting of hydrogen and alkyl groups having from 1 to 5 carbon atoms, the maximum number of carbon atoms in all said R groups being 10, and n is an integer having a value of 1 to 5, and B. the corresponding thiodialkylnitrile of the formula

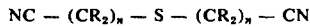

wherein R and n are as defined above, the maximum number of carbon atoms in all said R groups being 20, the weight ratio of said compound (A) to said compound (B) being in the range of 99:1 to 1:99, and a stabilizing amount of an organic phosphite of the formula

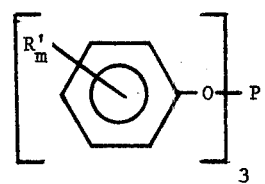

wherein R' is selected from the group consisting of hydrogen and alkyl groups having from 1 to 20 carbon atoms, and m is an integer having a value of 1 or 2.

10. The composition of claim 9 wherein the amount of said organic phosphite in said composition is in the approximate range of 0.01 to 5 weight percent.

11. The composition of claim 9 wherein the weight ratio of said compound (A) to said compound (B) is in the approximate range of 60:40 to 90:10.

12. The composition of claim 9 wherein said R' is alkyl.

13. The composition of claim 9 wherein said R' is selected from the group consisting of hydrogen and alkyl groups of from 6 to 12 carbon atoms.

14. The composition of claim 13 wherein said R' is alkyl.

15. The composition of claim 14 wherein said organic phosphite is tris(4-n-nonylphenyl) phosphite.

16. The composition of claim 9 wherein said compound (A) is 3-mercaptopropionitrile and said compound (B) is 3,3'-thiodipropionitrile.

* * * * *